United States Patent [19]

Klemt et al.

[11] Patent Number: 5,677,192
[45] Date of Patent: Oct. 14, 1997

[54] ELECTROCHEMILUMINESCENCE ASSAY

[75] Inventors: Volker Klemt, Weilheim; Günter Müller, Peissenberg; Ulrich Neumann; Ursula Giesen, both of Weilheim; Nicholas Hoyle, Tutzing, all of Germany

[73] Assignee: Boehringer Mannheim GmbH, Mannheim, Germany

[21] Appl. No.: 545,658

[22] PCT Filed: Apr. 27, 1994

[86] PCT No.: PCT/EP94/01328

§ 371 Date: Mar. 18, 1996

§ 102(e) Date: Mar. 18, 1996

[87] PCT Pub. No.: WO94/25853

PCT Pub. Date: Nov. 10, 1994

[30] Foreign Application Priority Data

| May 3, 1993 | [DE] | Germany | 43 14 547.7 |
| Sep. 25, 1993 | [DE] | Germany | 43 32 697.8 |
| Jan. 20, 1994 | [DE] | Germany | 44 01 577.1 |

[51] Int. Cl.$^6$ ................................................. G01N 21/76
[52] U.S. Cl. .................... 436/172; 250/361 C; 422/52
[58] Field of Search .................. 436/172; 250/361 C; 422/52

[56] References Cited

U.S. PATENT DOCUMENTS 4,927,769  5/1990  Chang et al. ........................ 436/518

FOREIGN PATENT DOCUMENTS

| 96749 | 12/1983 | European Pat. Off. . |
| 9005296 | 5/1990 | WIPO . |
| 9005302 | 5/1990 | WIPO . |

OTHER PUBLICATIONS

H. Karatani et al, "Electrogenerated Chemiluminescence of Cyclic Hydrazides in an Alkaline Brij35 Micellar System" Journal of Photochemistry and Photobiology A: Chemistry, 54 No month available (1990) 311–319.

*Primary Examiner*—Kathryn L. Gorgos
*Assistant Examiner*—John S. Starsiak, Jr.
*Attorney, Agent, or Firm*—Felfe & Lynch

[57] ABSTRACT

Method for measuring electrochemiluminescent phenomena using certain detergents and, if necessary, alkali chlorides and reagents suitable for this purpose.

16 Claims, No Drawings

ELECTROCHEMILUMINESCENCE ASSAY

This application is the U.S. National Stage (filed under 35 U.S.C. 371) of International application No. PCT/EP 94/01328, filed 27, Apr. 1994.

Subject matter of the invention are methods for measuring electrochemiluminescent phenomena, methods for detecting an analyte using said methods, reagent solutions which can be used in said method and an apparatus particularly suitable for carrying out said method.

Methods for measuring electrochemiluminescent phenomena have been known for some years. Such methods make use of the ability of special metal complexes to achieve, by means of oxidation, an excited state from which they decay to the ground state, emitting electromagnetic radiation. Methods of this kind and suitable metal complexes are described in WO 86/02734, for example.

This technology has continually become more sophisticated. In WO 90/05296, an amine, preferably tripropylamine, which is a strong reducing agent when oxidized, is added to the test composition. The electrochemical reaction occurs in an electrolyte where the electrochemiluminescence (ECL) moiety, i.e. the metal complex able to emit electromagnetic radiation and the amine can be oxidized. The description mentions phosphate buffer at a pH of 6-9, preferably 7-7.5, as a suitable electrolyte in aqueous solution.

To increase the electromagnetic radiation, WO 90/05302 proposes to add Triton X-100 or Triton N-401, a detergent, to this test composition. WO 90/05411 describes an improved apparatus for measuring ECL.

Further, it has become possible to use the technology for detecting analytes by coupling electrochemiluminescent labels to analytes, analyte analogs or analyte-specific substances. The electrochemiluminescence was used to determine the quantity of analyte present. The description mentions in particular immunoassays where conventionally used labels are replaced by electrochemiluminescent labels.

Further improvements and applications of this technology are described in WO 87/06706, WO 89/04392, WO 89/10552, WO 89/10551, WO 90/05301, and WO 90/11511. The disclosures of these publications are assumed to be known.

It was, hence, an object of the present invention to improve said known methods, especially with respect to the sensitivity of the analyte detection in combination with electrochemiluminescence assay procedures.

Subject matter of the invention is a method of measuring electrochemical phenomena in a solution or a solid phase contiguous with the solution, wherein the solution is a detergent selected from the group consisting of fat alcohol ethoxylate, Plantaren, and octylglucoside or a mixture thereof.

Moreover, subject matter of the invention is also a method of detecting an analyte using said method and suitable reagents for carrying out said method.

The subject matter of the invention is a teaching based on the above listed prior art. The fundamentals of electrochemiluminescent procedures are described in greater detail in these prior art documents. Instruments for measuring electrochemiluminescence comprise a measuring unit with the container for a reagent solution, at least two electrodes (a working electrode and a counter electrode) which are in contact with the reagent solution during the measurement, and a detector to measure the light generated in the electrochemiluminescent process. Usually, an initial voltage (prepolarization) is first applied to the solution. Subsequently, this voltage is increased via the redox potential of a substance, e.g. an amine, contained in the solution. The so oxidized substance excites a material, e.g. certain ruthenium complexes, which are capable of producing chemiluminescence, to emit light. The amount of light received by a detector within a given time interval is a measure for the presence of the quantity of an electrochemiluminescent material. Provided the electrochemiluminescent material is a label for an analyte, an analyte analog or an analyte-specific substance, e.g. in an immunoassay, the light received is a measure for the presence of the analyte.

Experience has shown that the commonly used detergent Triton X-100, known from WO 90/05302, which is usually employed in combination with the detergent Tween 20, does not produce optimal results. On the one hand, Triton X-100 is difficult to degrade and, hence, not beneficial to the environment. On the other hand, experience has surprisingly shown that certain other detergents improve the ECL method as compared to Triton X-100. These special detergents are used to increase the signal yield, to improve the signal/noise ratio thus achieving higher a sensitivity of the detection and to lower the lower detection threshold, and, finally, to achieve a better precision.

Suitable detergents are those from the group consisting of fat alcohol ethoxylates, including, for example, Polidocanol (dodecylpoly-(ethylene glycol ether)$_n$), C14-E09 (poly(ethylene glycol ether)$_n$), Genapol (isotridecylpoly (ethylene glycol ether)$_n$), C8-E09 (octyl alcohol poly (ethylene glycol ether)$_n$); Plantaren® (alkylpolyglucoside) and octylglucoside (octyl-beta-D-glucopyranoside) or a mixture thereof have proven to be particularly useful. The detergents are used in concentrations ranging between 0.001 and 1.0 %. The optimal concentration can be easily determined for each detergent. The most suitable concentrations are those ranging between 0.1 and 0.5 %.

Sodium azide at a concentration of 5–10 mM is normally used as a preservative in this test composition. Experience has shown that this environmentally harmful agent can be replaced by bioban or oxaban which are by far more beneficial to the environment than azide.

Surprisingly, these stabilizers have another positive effect on the ECL process, namely an increase of the measuring signal. Oxaban and bioban are used in concentrations of 0.01 to 1%, preferably 0.1 to 0.5 %.

The method in accordance with the invention for measuring electochemical phenomena in a solution or a solid phase contiguous with the solution can be carried out at temperatures above the freezing point of the solution, but less than 40° C.

The sensitivity can further be increased by applying a square-wave voltage to the measuring unit. This means the initial voltage is directly increased (within a maximum of 0.4 seconds) to the value of the end voltage. During the excitation time, this voltage is kept essentially constant. After this time, this voltage is directly reduced to a value below the redox potential of the system. Moreover, this measure also improves the dynamic measuring range, i.e. the range in which analyte concentrations of a determined immunoassay can be measured. If lower temperatures are used, the addition of salt is a preferred measure.

It has proven to be advantageous to limit the square-wave end voltage applied to the working electrode (compared to Ag/AgCl) to a maximum value between the redox potential of the oxidizable substance and 2.2 V. A particularly preferred voltage ranges between 1.2 and 2.2 V. Particularly preferred is a value of 1.4 V. These values apply if the electrodes used are made of platinum or gold.

If the commonly used ramp voltage, for example a delta voltage, is applied, the end voltage (compared to Ag/AgCl) is limited to a maximum of 3.0 V.

Surprisingly, the signal could also be increased by applying to the working electrode an initial voltage between +400 and −400 mV compared to an Ag/AgCl electrode prior to generating electrochemiluminescence. A particularly preferred voltage ranges between 0 mV and +200 mV. Again, these values apply if the electrodes used are made of platinum or gold. The potentials for the electrode materials can be easily calculated.

Further, the signal can also be increased by adjusting a pH between 6.5 and 9.0, preferably between 6.5 and 7.5, more particularly a pH of 6.8. This is advantageously done by using a pH buffer suitable for this range. Additionally, the solution may also contain one or several alkali or earth alkali halogenides at a concentration of 0.05 mmol/l to 0.5 mol/l. Sodium chloride is the preferred material.

The aforementioned measures per se already significantly improve known assays. Moreover, it is possible to further significantly increase the sensitivity and/or the dynamic measuring range of analyte detection assays by combining these measures.

When the detection sensitivity of analytes, for example, in immunoassays according to the sandwich principle or the competitive method is increased, the method or the apparatus used can be further simplified. It is, for example, possible to use a photodiode as detector, to simplify system calibration, to increase the number of tests done per time unit since the measuring time is reduced with an increased signal, or to reduce the sample volumes.

Another subject matter of the invention is a reagent solution for measuring electrochemical phenomena and especially for detecting analytes which comprises an electrochemically oxidizable amine or is a strong reducing agent when oxidized. The solution contains a detergent selected from the group consisting of fat alcohol ethoxylates, Plantaren® and octylglucoside or a mixture thereof. In addition, it can contain an alkali chloride at a concentration of 0.1 mmol/l to 0.5 mol/l and/or have a pH between 6.8 and 8.0. Further, the solution can also contain conventionally used additional substances, for example buffer substances, stabilizers and preservatives.

The reagent solution is preferably stabilized with bioban or oxaban.

An apparatus for carrying out detections by means of electrochemiluminescence is described in great detail in Example 1 of WO 90/05302, for example. Moreover, such an apparatus can comprise means for cooling the measuring unit and/or a liquid container to temperatures between 0 and 25° C., if the assay is to be carried out at such low temperatures. The measuring unit is understood to be a cell in which the electrochemiluminescence is measured. The liquid vessel can be a storage container, but also a feeding device, e.g. a tube for the reagent solution which is contained in the measuring unit during the measurement.

Also subject matter of the invention is a method for detecting an analyte using an electrochemiluminescent label, wherein one of the above listed methods for measuring electrochemiluminescent phenomena is employed.

The following examples are intended to further illustrate the invention:

EXAMPLE 1

The effect of the detergent used in accordance with the invention was determined in a series of experiments. In order to determine the influence of the detergents on the generation of the signal independently of the individual test parameters, i.e. the analytes to be determined, streptavidin-coated magnetic particles to which a biotinylated or ruthenylated antibody was attached, was used (HSAP: "hot streptavidin particle").

An apparatus as described in example 1 of WO 90/05302 which also contained a permanent magnet in its measuring cell (Origen 1.0 by IGEN, Rockville, U.S.A. or Magnalyser) was used for the measurement. This instrument also contains a photomultiplier, a petentiostat, an electrochemical flow-through cell, liquid transfer agents and a 50-tube sample rotor.

The following substances were combined in a reagent tube to carry out the analysis:

| | |
|---|---|
| HSAP (lyophilized HSAP was dissolved in a Tris/polydocanol buffer (100 mm; 0.1%) pH 9.0 to give a working solution of 600 μg/ml) | 50 μl |
| PBS buffer (50 mM KH$_2$PO$_4$; 100 mM NaCl; 0.1% BSA; pH 7.0) | 200 μl |

Reagent solution (200 mM KH$_2$PO$_4$ buffer; 100 mM TPA; pH 7.5; for each reagent tested)

This mixture was pipetted into a measuring tube and then transferred into the measuring cell. The HSAP were washed with the buffer (AB) and the signal yield was measured in this buffer.

The antibody used was biotinylated with biotin-DDS (biotinyl-amino-3,6-dioxaoctanoyl-aminocarbonyl-heptanoic acid-N-hydroxysuccinimide ester). (Tris) (2,2'-bipyridil) ruthenium chloride hexahydrate was bound to the antibody by using DSS (disuccinyl suberate).

The streptavidin-coated magnetic particle was purchased from Deutsche Dynal GmbH, Germany (Dynabeads M-280 Streptavidin).

The buffer (AB) used in the measurement was composed as follows:

| | |
|---|---|
| KH$_2$PO$_4$ * 2H$_2$O | 0.2 M |
| KOH | 0.076 M |
| NaCl | 0.05 mM |
| TPA (tripropylamine) | 0.1 M |
| Detergent | concentrations as stated in the table |
| Oxaban/bioban | 0.1/0.3% |
| pH | 7.5 |

The controls used were the commonly known detergents Tween 20 and Triton X-100, each at a concentration of 0.05%. To have a reference, the signal yield obtained with this detergent given in Table 1 was considered to be 100%. To have another measurement value, the non-specific signal yield in the buffer (AB) was determined and used to calculate the ratio of the HSAP/AB signal yield. This ratio between the signal yield with and without HSAP is a good indicator for the sensitivity of the assay. From the results given in Table 1, it can be clearly understood that the detergents of the invention are most suitable.

Polidocanol and C8-EO9 show the best effect on the HSAP/AB ratio. Detergents other than Tween/Triton X-100 negatively affect the signal yield.

TABLE 1

Detergents tested for the ECL assay buffer
Electrode: BPt3
PMT 700 V

| Detergent in the buffer | HSAP [%] | HSAP/AB [%] |
|---|---|---|
| 0.05% Tween | 100 | 100 |
| 0.05% Triton | | |
| 0.1% Polidocanol | 295.1 | 414.5 |
| 0.4% C14-E09 | 289.2 | 292.8 |
| 0.2% C14-E09 | 346.2 | 308.2 |
| 0.1% C14-E09 | 382 | 343.2 |
| 0.05% C14-E09 | 402.5 | 342.4 |
| 0.4% Genapol | 360.1 | 117.8 |
| 0.2% Genapol | 377.2 | 129.6 |
| 0.1% Genapol | 386.5 | 126 |
| 0.05% Genapol | 361.5 | 140.1 |
| 0.4% C8-E09 | 481.4 | 530.3 |
| 0.2% C8-E09 | 402 | 394.7 |
| 0.1% Plantaren | 219.1 | 200.7 |
| 0.05% Plantaren | 270.6 | 276.3 |
| 0.025% Plantaren | 295.3 | 292.1 |
| 0.2% Octylglucoside | 286.8 | 390.8 |
| 0.2% Tween 20 | 106.9 | 176.3 |
| 0.1% Tween 20 | 114.9 | 184.9 |
| 0.05% Tween 20 | 124.8 | 213.2 |
| 0.2% Triton X-100 | 62.6 | 68.8 |
| 0.1% Triton X-100 | 83 | 154.3 |
| 0.05% Triton X-100 | 115.6 | 195.4 |
| 0.2% C16-E09 | 17.3 | 36.8 |
| 0.05% C16-E09 | 50 | 98 |
| 0.2% Dodecyl maltoside | 17.7 | 50 |
| 0.1% Dodecyl maltoside | 46.9 | 112.5 |
| 0.2% SDS | 4.1 | 5.6 |
| 0.1% SDS | 22.9 | 32.9 |
| 0.2% Ralufon 3–14 | 27.3 | 29 |
| 0.1% Ralufon 3–14 | 27.8 | 31.3 |

Names and abbreviations of the detergents used
C8-E09: Octylalcoholpoly(ethylene glycol ether)$_n$
C14-E09: Poly(ethylene glycol ether)$_n$
C16-E09: Cetylpoly(ethylene glycol ether)$_n$
Dodecyl maltoside: Dodecyl-β-D-glucopyranosyl(1→4)α-D-glucopyranoside
Genapol: Isotridecylpoly(ethylene glycol ether)$_n$
Octylglucoside: Octyl-β-D-glucopyranoside
Plantaren: Alkylpolyglucoside (C14–C16)
Ralufon 3–14: n-Tetradecyl-n,n-dimethyl-3-amino-1-propane sulfate
SDS: Sodium lauryl sulfate
Polidocanol: Dodecylpoly(ethylene glycol ether)$_n$
Triton X-100: Octylphenolpoly(ethylene glycol ether)$_n$
Tween: Poly(oxyethylene)n-sorbitane-monolaurate

EXAMPLE 2

A parameter-independent test (HSAP) was used to test the effects of the cell temperature on the signal recovery and the dynamics if a ramp voltage was used at 28–35° C. in the measuring cell in dependency upon NaCl.

The test was carried out as described for example 1. The buffer (AB) was replaced by buffer BMG 2 which had the following composition:

| | |
|---|---|
| $H_3PO_4$ | 0.2 M |
| Polidocanol | 0.1% |
| Oxaban | 0.1% |
| Tripropylamine | 0.16 M |
| KOH | 0.12 M |
| pH | 6.8 |
| NaCl | concentrations as stated in the table |

The results are given in table 2. An increase of the temperature and the salt concentration also leads to an increase of the ECL signals which were obtained with buffer (BMG2) alone and with HSAP. The HSAP/AB, HSAP/FC and FC/AB ratios are almost temperature-independent, but depend upon the salt concentration.

TABLE 2

| Temperature (°C.) | 28 | 30 | 35 |
|---|---|---|---|
| a) Temperature/salt dependency of the ECL signals | | | |
| Salt concentration | NaCl 0% | NaCl 0% | NaCl 0% |
| BMG 2 | 2479 | 2111 | 3165 |
| FC | 4378 | 3426 | 6856 |
| HSAP | 3160000 | 2550000 | 3610000 |
| HSAP/BMG 2 | 1257 | 1208 | 1141 |
| HSAP/FC | 722 | 744 | 626 |
| FC/BMG 2 | 1.77 | 1.62 | 2.17 |
| Salt concentration | NaCl 0.2% | NaCl 0.2% | NaCl 0.2% |
| BMG 2 | 1963 | 2169 | 2930 |
| FC | 5072 | 4281 | 4137 |
| HSAP | 3940000 | 4030000 | 4450000 |
| HSAP/BMG 2 | 2007 | 1858 | 1519 |
| HSAP/FC | 777 | 941 | 1076 |
| FC/BMG 2 | 2.58 | 1.97 | 1.41 |
| Salt concentration | NaCl 0.9% | NaCl 0.9% | NaCl 0.9% |
| BMG 2 | 2208 | 2367 | 3610 |
| FC | 5280 | 4954 | 7487 |
| HSAP | 5130000 | 5940000 | 6940000 |
| HSAP/BMG 2 | 2323 | 2510 | 1927 |
| HSAP/FC | 972 | 1199 | 927 |
| FC/BMG 2 | 2.39 | 2.09 | 2.06 |
| Salt concentration | NaCl 1.8% | NaCl 1.8% | NaCl 1.8% |
| BMG 2 | 2691 | 2970 | 4453 |
| FC | 5805 | 6129 | 6507 |
| HSAP | 4200000 | 4750000 | 5830000 |
| HSAP/BMG 2 | 1561 | 1599 | 1309 |
| HSAP/FC | 724 | 775 | 896 |
| FC/BMG 2 | 2.16 | 2.06 | 1.46 |
| b) Evaluation in %, based on 28° C., 0% NaCl | | | |
| Salt concentration | NaCl 0% | NaCl 0% | NaCl 0% |
| BMG 2 | 100.0 | 85.2 | 127.7 |
| FC | 100.0 | 78.3 | 156.6 |
| HSAP | 100.0 | 80.7 | 114.2 |
| HSAP/BMG 2 | 100.0 | 94.8 | 89.5 |
| HSAP/FC | 100.0 | 103.1 | 72.9 |
| FC/BMG 2 | 100.0 | 91.9 | 122.7 |
| Salt concentration | NaCl 0.2% | NaCl 0.2% | NaCl 0.2% |
| BMG 2 | 79.2 | 87.5 | 118.2 |
| FC | 115.9 | 97.8 | 94.5 |
| HSAP | 124.7 | 127.5 | 140.8 |
| HSAP/BMG 2 | 157.5 | 145.8 | 119.1 |
| HSAP/FC | 107.6 | 130.4 | 149.0 |
| FC/BMG 2 | 146.3 | 111.8 | 80.0 |
| Salt concentration | NaCl 0.9% | NaCl 0.9% | NaCl 0.9% |
| BMG 2 | 89.1 | 95.5 | 145.3 |
| FC | 120.6 | 113.2 | 171.0 |
| HSAP | 162.3 | 188.0 | 210.6 |
| HSAP/BMG 2 | 182.3 | 196.9 | 151.2 |
| HSAP/FC | 134.6 | 166.1 | 128.4 |
| FC/BMG 2 | 135.4 | 118.5 | 117.7 |
| Salt concentration | NaCl 1.8% | NaCl 1.8% | NaCl 1.8% |
| BMG 2 | 108.6 | 119.6 | 179.6 |
| FC | 132.6 | 140.0 | 148.6 |
| HSAP | 132.9 | 150.3 | 184.5 |
| HSAP/BMG 2 | 122.4 | 125.5 | 102.7 |
| HSAP/FC | 100.2 | 107.4 | 124.1 |
| FC/BMG 2 | 122.1 | 116.9 | 82.7 |

BMG 2: Control with sample buffer BMG 2
FC: Control with free conjugate (biotinylated and ruthenylated antibody)
HSAP: hot streptavidin particle If the temperature is reduced to less than 20° C., it is necessary to add an alkali chloride and to adjust the solution to a preferred pH value between 7.25 and 7.75.

EXAMPLE 3

Detection of $T_3$

An immunoassay for the detection of tri-iodine thyronin ($T_3$) was used to compare the test composition of the invention BMG 1 with the prior-an test composition (BMG 0):

The reagent solutions had the following composition:

| Reagent | BMG 0 | BMG 1 |
|---|---|---|
| $KH_2PO_4 \times 2 H_2O$ | 0.2 M | 0.2 M |
| $H_3PO_4$ | — | — |
| Detergent | Triton X-100 0.005% Tween 0.05% | Polidocanol 0.1% |
| Preserving agent | $NaN_3$ 7.8 mM | Oxaban 0.1% |
| Tripropylamine | 0.1 M | 0.1 M |
| KOH | 0.076 M | 0.076 M |
| pH | 7.5 | 7.5 |

The following additional reagents were also used:

| | | |
|---|---|---|
| HEPES buffer 7.0: | HEPES-Na 7.0 | 0.1M |
| | | 0.06% ANS |
| | | 0.1% Bovine IgG |
| | | 0.5% Byco |
| | | 50 mM NaCl |
| PAB-RU | (ruthenylated polyclonal antibody) (Tris) (2,2'-bipyridyl)ruthenium chloride hexahydrate via DDS bound to PAB against $T_3$ in HEPES buffer 7.0 | 100 ng/ml |
| PH-BI | ($T_3$-polyhapten biotinylated) PH PAB ←→K-IgG(DE)BOC-$T_3$-1 Bi in HEPES buffer 7.0 | 600 ng/ml |

Samples:

Standard a–e

Concentration $T_3$:

a: 0.24 ng/ml b: 0.88 ng/ml c: 1.90 ng/ml d: 3.05 ng/ml e: 6.65 ng/ml 3 human sera 2 human sera without/with 500 mg/dl hemoglobin (Hb)

Streptavidin-coated magnetic particles:

| | |
|---|---|
| Dynabeads M-280 Streptavidin (Deutsche Dynal GmbH, Germany) in HEPES buffer 7.0 | 600 µg/ml |

The following substances were combined to carry out the detection reaction:

| | |
|---|---|
| PAB-Ru | 50 µl |
| Dynabeads M-280 | 50 µl |
| Sample | 30 µl |
| PH-Bi | 50 µl |
| BMG 0 or 1 | 500 µl |

This mixture was incubated for 16 minutes at 28° C. and then transferred to the measuring cell which was brought to a temperature of 28° C. The particles were washed with BMG 0 or 1 depending on the test mixture and then measured. A delta ramp voltage was then applied. The measuring voltage was 0.565 V and the PMT 720 mV.

The results are summarized in table 3. It was found that the hemoglobin interference which can be observed in BMG 0 is no longer present in BMG 1. This does not affect the lower detection limit.

TABLE 3

| | BMG 0 | BMG 1 |
|---|---|---|
| LDL (2s) | 0.3 ng/ml | 0.3 ng/ml |
| Human serum without Hb | 100% | 100% |
| Human serum with Hb | 307% | 106% |

LDL (2s) = Lower detection limit

EXAMPLE 4

Detection of HBsAg

In a sandwich immunoassay, the test composition BMG 1 in accordance with the invention was used to detect HBsAg. The result was compared to the one obtained with BMG 0. BMG 0 and 1 had the compositions given in example 3.

The following reagents were used:

| | | |
|---|---|---|
| HEPES buffer pH 7.5: | HEPES-Na | 0.05M |
| | Bovine serum albumin | 1% |
| | Genapol X 080 | 0.1% |
| | Bovine(R)-IgG | 0.1% |
| | Mouse-IgM | 10 µg/ml |
| | CAM (chloracetamide) | 0.1% |
| | MIT (methylisothiazolon) | 0.01% |
| AB-Bi | (antibody biotinylated with biotin-DDS) MAB<HBs>M5A10-IgG-Bi (DDS) 1:7.5 in HEPES buffer pH 7.5 | 300 ng/ml |
| TAG | (ruthenylated antibody) MAB<HBs>M5A10-F(ab')2-BPRU (Tris) (2,2'-bipyridyl)ruthenium chloride hexahydrate bound to the monoclonal antibody using DDS against HBsAg (F(ab') fragment) in HEPES buffer pH 7.5 | 500 ng/ml |

Samples:

Standard a–h

Concentration HBsAg a: 0 U/ml b: 0.22 U/ml c: 0.52 U/ml d: 1.08 U/ml e: 2.30 U/ml f: 4.50 U/ml g: 10.30 U/ml h: 22.20 U/ml Streptavidin-coated magnetic particles:

| | |
|---|---|
| Dynabeads M-280 streptavidin in HEPES buffer pH 7.5 | 600 µg/ml |

The following substances were combined for the detection reaction:

| | |
|---|---|
| Dynabeads M-280 | 50 µl |
| AB-Bi | 50 µl |
| TAG | 40 µl |
| Sample | 50 µl |
| HEPES buffer pH 7.5 | 20 µl |
| BMG 0 or 1 | 150 µl |

The mixture was incubated for 16 minutes at 28° C. and then transferred into a measuring cell which had been heated up to 28° C. The particles were washed with BMG 0 or 1 and then measured.

The results are summarized in table 4. The use of BMG 1 significantly improved the lower detection limit. The CV was also reduced as compared to BMG 0. The ratio of the values of the standard samples h to a of the calibration curve is increased for BMG 1 which allows an improved differentiation of the calibration curve.

TABLE 4

|  | BMG 0 | BMG 1 |
|---|---|---|
| LDL [E/ml] | 0.21 | 0.06 |
| Standard h/a | 40 | 78 |
| CV [%] | 6.9 | 4.3 |

LDL: Lower detection limit
CV: Coefficient of variation

EXAMPLE 5

Detection of TSH

The test compositions BMG 1 and BMG 1 without oxaban as compared to the prior-art test composition BMG 0 was used in a sandwich immunoassay for the detection of TSH (thyroid-stimulating hormone). BMG 0 and BMG 1 had the compositions given in example 3.

Thyroid-stimulating hormone (THS) was determined in a Sandwich immunoassay. The assay was performed with the aid of an apparatus as described in example 1.

The following substances were combined for the detection reaction:

| Incubation buffer | | 50 µl |
|---|---|---|
| (containing 6.06 g/l Tris × HCl; | | |
| 1 g/l chloracetamide; | | |
| 0.1 g/l methylisothiazolon, pH 8.0; | | |
| 50 g/l bovine serum albumin; | | |
| 10 g/l R-IgG) | | |
| Streptavidin-coated magnetic particles | 600 µg/ml | 40 µl |
| (Dynal, 2.8 µm) | | |
| in the incubation buffer | | |
| monoclonal antibody (MAB) | 3.0 µg/ml | 40 µl |
| to TSH biotinylated with DSS | | |
| (disuccinidyl suberate) | | |
| in the incubation buffer | | |
| TAG: | 1.2 µg/ml | 40 µl |
| (Tris) (2,2'-bipyridyl)ruthenium chloride | | |
| hexahydrate bound with DSS to the MAB to TSH | | |
| in the incubation buffer | | |
| Sample liquid or standard | | 50 µl |
| Resuspension (addition of reagent solution (BMG1)) | | 100 µl |

This mixture was incubated for 16 minutes at room temperature (21° C.) and then transferred to the measuring cell which had been brought to room temperature. The immobilized particles were washed with reagent solution BMG1 and measured in BMG1.

The samples used were the standards a–e with TSH concentrations of a: 0 µU/ml
b: 0.39 µU/ml
c: 3.54 µU/ml
d: 12.4 µU/ml
e: 44.3 µU/ml The results are summarized in table 5. BMG 1, as compared to BMG 0, shows an improved detection limit. The addition of the preservative agent oxaban further reduces the lower detection threshold. In both cases, the coefficient of variation is also significantly improved (BMG 1±oxaban).

TABLE 5

|  | BMG 0 | BMG 1 | BMG 1 without oxaban |
|---|---|---|---|
| LDL (2s) [mIU/ml] | 0.049 | 0.028 | 0.041 |
| CV [%] | 3.35 | 2.28 | 2.38 |

The abbreviations have the same meanings as those given in example 4.

We claim:

1. In a method for measuring electrochemiluminescence of a component capable of generating electrochemiluminescence by contacting said component with a solution which contains an oxidizable amine, applying an electrical voltage to said component and said solution to induce electrochemiluminescence, and detecting induced electrochemiluminescence, the improvement comprising adding at least one detergent selected from the group consisting of a fatty acid alcohol ethoxylate, alkylpolyglucoside, and octylglucoside to said solution.

2. The method of claim 1, wherein said component is attached to a solid phase.

3. The method of claim 1, wherein said component is in solution.

4. The method of claim 1, wherein said fatty acid alcohol ethoxylate is dodecylpoly-(ethylene glycol ether)n, poly (ethylene glycol ether)n, isotridecylpoly (ethylene glycol ether)n, or octyl alcohol poly(ethylene glycol ether)n.

5. The method of claim 1, wherein said solution further comprises at least one alkali halide.

6. The method of claim 1, wherein said solution further comprises at least one earth alkali halide.

7. The method of claim 1, wherein said solution has a pH of from about 6.5 to about 9.0.

8. The method of claim 1, comprising inducing said electrochemiluminescence by applying a maximum square-wave voltage of 2.2. V.

9. The method of claim 1, comprising inducing said electrochemiluminescence by applying a maximum ramp voltage of 3.0 volts.

10. In a method for determining an analyte in a sample by contacting said sample with an electrochemiluminescently labelled substance selected from the group consisting of labelled analyte analog, and a labelled analyte specific substance and determining electrochemiluminescence as a determination of said analyte in said sample, the improvement comprising adding at least one detergent selected from the group consisting of a fatty acid alcohol ethoxylate, alkylpolyglucoside, and octylglucoside to said sample.

11. The method of claim 10, wherein said fatty acid alcohol ethoxylate is dodecylpolyethylene glycol ether)n, isotridecylpoly (ethylene glycol)n, or octyl alcohol poly (ethylene glycol ether)n.

12. The method of claim 10, further comprising adding at least one alkali halide to said solution.

13. The method of claim 10, further comprising adding at least one earth alkali earth halide to said solution.

14. The method of claim 10, wherein said solution has a pH of from about 6.5 to about 9.0.

15. The method of claim 10, comprising determining electrochemiluminescence by applying a maximum voltage of 2.0 volts.

16. The method of claim 10, comprising determining electrochemiluminescence by applying a square voltage of 3.0 volts.

* * * * *

UNITED STATES PATENT AND TRADEMARK OFFICE
CERTIFICATE OF CORRECTION

PATENT NO. : 5,677,192
DATED : October 14, 1997
INVENTOR(S) : Volker Klemt, et al.

It is certified that error appears in the above-indentified patent and that said Letters Patent is hereby corrected as shown below:

In column 4, line 11, change "petentiostat" to read as -- potentiostat --.

In column 4, line 19, change "mm" to read as -- mM --.

In column 6, line 66, change "an" to read as -- art --.

In column 9, line 54, change "BMG1," to read as -- BMG1. --.

Signed and Sealed this

Twenty-seventh Day of March, 2001

Attest:

NICHOLAS P. GODICI

Attesting Officer

Acting Director of the United States Patent and Trademark Office